United States Patent [19]

Kychakoff et al.

[11] Patent Number: 5,010,827
[45] Date of Patent: Apr. 30, 1991

[54] APPARATUS FOR DETECTING CARRYOVER PARTICLES IN THE INTERIOR OF A FURNACE

[75] Inventors: George Kychakoff, Maple Valley, Wash.; Gene P. Ort, Spring, Tex.

[73] Assignee: Wyerehaeuser Company, Tacoma, Wash.

[21] Appl. No.: 521,082

[22] Filed: May 8, 1990

[51] Int. Cl.$^5$ ................................................ F23N 5/00
[52] U.S. Cl. .................................... 110/185; 110/186; 236/15 E; 431/76
[58] Field of Search ........................ 431/76; 236/15 E; 122/379; 110/185, 186; 358/106

[56] References Cited

U.S. PATENT DOCUMENTS

| | | | |
|---|---|---|---|
| 3,814,570 | 6/1974 | Guigues et al. | 431/76 |
| 3,830,969 | 8/1974 | Hofstein . | |
| 4,359,950 | 11/1982 | Leffler et al. | 236/15 E |
| 4,539,588 | 9/1985 | Ariessohn et al. . | |
| 4,690,634 | 9/1987 | Herngren et al. . | |
| 4,737,844 | 4/1988 | Kohola et al. . | |
| 4,814,868 | 3/1989 | James . | |

OTHER PUBLICATIONS

An article by Mark J. Anderson et al., entitled "Monitoring of Recovery Boiler Interiors Using Imaging Technology", published in Apr. of 1989 by a division of Weyerhaeuser Co.
An article published in Sep. of 1987 by the Sensor & Simulation Products division of Weyerhaeuser Co. entitled, "System Insight-The Value of the Smelt Bed Imaging System".

Primary Examiner—Edward G. Favors
Attorney, Agent, or Firm—Klarquist, Sparkman, Campbell, Leigh & Whinston

[57] ABSTRACT

An apparatus for detecting the presence of carryover particles in an upper region of a furnace, such as a smelt bed boiler, includes plural spaced apart detectors. These detectors monitor discrete portions of the interior of the furnace for the purpose of detecting carryover particles in such monitored portions. Signals indicative of the carryover particles are processed to obtain a count of the carryover particles. The carryover particle count may then be displayed. For example, the signals from all of the detectors may be averaged with trends and overall changes in count rates then displayed. In addition, the counts from the individual detectors may also be displayed to assist an operator in locating the source of excessive carryover particles in the furnace. An image sensor, such as a charged coupled device (CCD) detector, may be used to provide a visual display of detected carryover particles. The information on carryover particle count may be used in controlling parameters affecting the performance of the furnace directly, or indirectly by way of operator input.

9 Claims, 4 Drawing Sheets

APPARATUS FOR DETECTING CARRYOVER PARTICLES IN THE INTERIOR OF A FURNACE

BACKGROUND OF THE INVENTION

The present invention relates to the detection of carryover particles in a furnace, such as a smelt bed boiler, and also to the use of information concerning detected carryover particles in the control of the furnace.

In general, carryover particles may be defined as "out-of-place" burning particles that are traveling in a furnace or boiler in a region well above the hearth of the furnace. More specifically, carryover particles in smelt bed recovery boilers may be defined as the mass of burning particles passing a horizontal plane at an upper level of the boiler, such as at the "bull nose" level within the boiler. Burning particles which encounter steam tubes in such a recovery boiler are quenched and form hard deposits on the tubing. These hard deposits are difficult to clean or remove through the use of typical steam cleaning mechanisms in such boilers.

Figure 1:
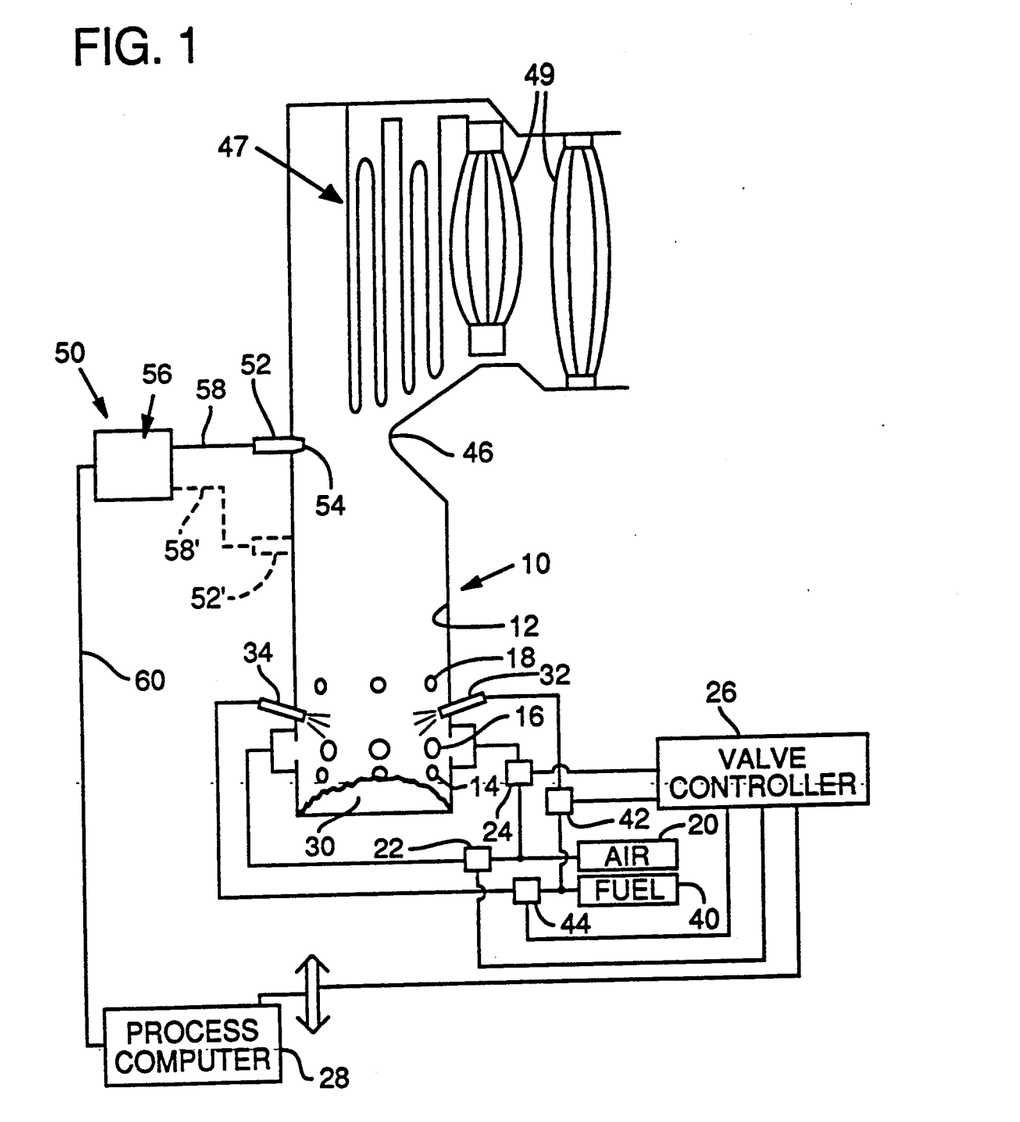
FIG. 1 is a schematic illustration of one form of a conventional recovery boiler which includes a carryover detection apparatus in accordance with the present invention.

A typical boiler is a liquor recovery unit used in mills for the manufacture of papermaking pulp. Such units typically require a substantial capital investment. In many cases the capacity of these boiler units limits the production of the pulp mill. A conventional liquor recovery unit is shown in FIG. 1 with a carryover particle detector system in accordance with the present invention. The recovery unit comprises a boiler 10 having a surrounding wall 12 through which water is carried for the purpose of steam generation. A typical modern unit of this type has a bottom area of about 50 square meters and a height of about 40 meters. Water tubes in the wall 12 and in the bottom of the incinerator or boiler are connected to a water drum, not shown, and, respectively, to a steam drum of a steam boiler. Through ports located about the circumference of the incinerator, normally at two or three different levels such as indicated by numbers 14, 16 and 18, combustion air is introduced into the boiler. Air is typically supplied into the boiler through these ports by large fans (not shown) with controlled dampers being used to adjust the air flow through these various ports. Schematically, the fans are represented in FIG. 1 as an air source 20 and some of the dampers are indicated as valves or dampers 22 and 24. A valve or damper controller 26, under the control of a process computer 28 and interface (not shown), control the operation of the various air supply dampers to control the flow of combustion air to the boiler. For example, to increase the rate of fuel combustion in the boiler, the amount of combustion air is typically increased. In addition, by supplying more air through selected ports than through other ports, an increase in the rate of consumption of fuel may be achieved in the regions of greater air supply to adjust the contour of a bed 30 at the bottom of the boiler.

Black liquor fuel enters the boiler through fuel nozzles 32, 34 as a coarse spray. Combustible organic constituents in the black liquor burn as the fuel droplets mix with air. Sodium sulfate in the fuel is chemically converted to sodium sulfide in the reducing zone of the boiler. The inorganic salts drop to the floor of the boiler to form a smelt bed 30, from which liquid is drained. The black liquor fuel is delivered from a fuel source 40 (from the pulp mill) and fed by conduits through respective valves 42, 44 to the nozzles 32 and 34 and hence to the combustion zone of the boiler. The process computer 28 and interface deliver suitable fuel control signals to the valve controller 26 for controlling the valves 42 and 44, and thus the supply of fuel.

It is desirable that combustion of substantially all of the black liquor fuel is carried out in the lower portion of the boiler 10, well below boiler steam tubes at an upper region of the boiler. However, in practice, dust particles formed in the hearth region of the boiler are carried along with flue gases upwardly through a restricted bull nose section 46 of the boiler. These particles in part adhere to the upper heat surfaces of the boiler. The dust typically contains sodium sulfate and sodium carbonate, but may also include other components to a varying extent. Under certain boiler or furnace conditions, such as resulting from disturbances in the air supply or perhaps due to a high bed volume in the boiler, uncombusted liquor fuel particles follow along with the upward gas flow. Such particles, as they burn, develop coatings on the heat surfaces which are removed only with great difficulty. Also, some of these particles burn as they contact the heat surfaces of the boiler and cause a sintering of other dust on the heat surfaces, again making the removal of these adhered particles very difficult. Thus, as hot gases from the combustion process entrain burning fuel particles and carry them upwardly, these particles may reach superheater tubes 47 and steam generator tubes 49 and may be deposited thereon. These tubes 47, 49 are conventionally used in such boilers for the generation of superheated steam for use in producing electrical power or for providing heat for other processes. As burning carryover particles impact these tubes, a buildup in the form of deposits occurs and tends to plug the passages between the tubes. Such a buildup reduces the heat transfer efficiency to the tubes and the boiler capacity. These deposits may eventually cause a shutdown of the boiler and also contribute to boiler tube corrosion.

For maintaining clean heat surfaces, including surfaces of the tubes 47 and 49, liquor recovery units are normally provided with a means for cleaning the heat surfaces. Such soot removal devices typically consist of pipes through which steam is injected while the pipes are being moved through the boiler. Even with these cleaning mechanisms, it is often necessary to stop the operation of the boiler for cleaning purposes. This often results in a loss of expensive pulp mill production time. In addition, these cleaning mechanisms are typically very effective at removing soft deposits on these tubes, but are much less efficient in removing the hard deposits formed by burning carryover particles.

The problems associated with the buildup of deposits from burning carryover particles on tubes of boilers have been recognized in the art. For example, U.S. Pat. No. 4,690,634 to Herngren, et al. describes an apparatus for counting burning carryover particles as they pass a detector. The count is used to indicate the occurrence of such carryover particles and/or in the control of the boiler operation. In the Herngren approach, a single optical detector is utilized which consists of a linear array of photo diodes (specifically 1024 diodes) arranged in rows. An optical lens is used to focus the diodes on a detection or focal plane, it being understood by the inventors that this detection plane is spaced only about two inches from the walls of the boiler. The resulting signal from the detector is amplified and compared to a threshold value which is used so that only signal peaks exceeding the threshold value are registered. The pulse width of the received signals is used in classifying the size of the particles. During a time interval, such as ten minutes, the device counts the number of detected carryover particle pulses within each particle size class, with the totals in the respective classes being converted to an analog current signal for delivery to a process computer.

The Herngren, et al. approach requires relatively complex and costly electronics to categorize carryover particles as to size. In addition, the use of a single detector positioned along one wall of a furnace, albeit with a linear array of photo diodes, permits in essence an examination of the boiler from one direction and, due to the limited depth of focal plane used in this approach, only a small region of the boiler interior is examined from this one direction. Consequently, localized disturbances in the smelt bed, which may result in the substantial production of carryover particles in a boiler region not within the single direction viewing utilized by Herngren, et al., may be missed.

Still another approach for monitoring the presence of carryover particles in a boiler is described in U.S. Pat. No. 4,814,868 to James. In the James approach, a single video camera imaging apparatus, such as of the type described in U.S. Pat. No. 4,539,588 to Ariessohn, et al., is disposed proximate to an upper portion of a recovery boiler for producing an analog video signal corresponding to the image of the interior of the boiler. The video signal is processed to eliminate noise and non-moving objects. A counter is used by James to count the occurrence of moving particles in the monitored region as a function of the relative magnitude of data points in the filtered signal and a predetermined threshold level. The particle count is incremented each time data points in the filtered signal exceed the threshold level. Such data points appear as a bright streak in the image and are caused by moving carryover particles. The imaging device of this patent is used to provide a video signal with a plurality of scan lines which are digitized and combined so as to discriminate between noise and burning particles. A display is used to display a visible image of the light emitting particles.

Through the use of a single camera, the James approach, like the approach of the Herngren patent, has a limited capacity to detect carryover particles other than along the wall which supports the camera. Due to the opaqueness of the environment in a typical boiler and the difficulty of detecting burning particles at significant distances (e.g. about three feet from the wall), the presence of carryover particles at distributed locations elsewhere in the boiler would tend to be overlooked by the Herngren, et al. and James devices.

In addition, the James approach is not understood to permit the discrimination between small carryover particles which are close to the camera and large carryover particles which are far away from the camera, as these particles appear to the camera to be of the same size.

Another system for detecting particles is disclosed in U.S. Pat. No. 3,830,969 to Hofstein. The Hofstein system utilizes a television camera for producing an image of a fluid sample with particulate matter therein. The image is processed to retain light points in the image which correspond to the moving particles. The resulting image is displayed on a CRT display or the like. The particulate matter is analyzed for characteristics such as movement, distribution, dimensions, number or concentration. There is no suggestion in this reference of operating such a system in the adverse environmental conditions present in a fuel fired furnace or boiler.

U.S. Pat. No. 4,737,844 to Kohola, et al. describes a system utilizing a video camera for obtaining a video signal which is digitized and filtered temporally and spacially. The digitized video signal is divided into signal subareas with picture elements belonging to the same subarea being combined into a continuous image area representing a certain signal level. The subareas are also combined into an integrated image with subsequent images being averaged to eliminate random disturbances. The averaged image is displayed on a display device. In an application described in this reference, the location, size and form of a flame front is determined from the image. This information on the flame front is used in the control of the combustion process. Although used in a furnace environment, this system is not directed toward the monitoring of carryover particles in a boiler.

In literature describing the device of the Ariessohn, et al. patent published in 1987, the smelt bed imaging system of such patent is described as providing clear, continuous images of the lower furnace char bed as well as of the deposit formation in the upper furnace. This literature does not set forth any details concerning the monitoring of deposit formations. Also, the device of the Ariessohn, et al. patent has been utilized in a commercially available product, called TIPS™, from Weyerhaeuser Company. This product relates to an electronic imaging device used in monitoring the temperature of the bed of furnaces, such as recovery boiler systems. An article by Mark J. Anderson, et al. entitled "Monitoring of Recovery Boiler Interiors Using Imaging Technology," published in April of 1989 by the Sensor and Simulation Production Division of Weyerhaeuser Company, describes this system in greater detail.

Although systems exist for use in monitoring the interior of recovery boilers and other furnaces, a need exists for an improved system for detecting carryover particles in the interior of such furnaces. This detected carryover particle information may then optionally be used in determining cleaning cycles for steam generation tubing and heat surfaces within the furnaces, for detecting abnormal conditions within the furnace which contribute to excessive carryover particle production, and for controlling the performance of the furnace so as to minimize the formation of such carryover particles.

SUMMARY OF THE INVENTION

An apparatus is described for detecting carryover particles in the interior of a furnace which includes at least one and preferably plural spaced apart discrete carryover particle detectors each directed toward an associated region of the interior of the furnace. These detectors are designed to detect the presence of carryover particles and to produce output signals upon the detection of such particles. A signal processor is coupled to the detectors for receiving the output signals and for producing a count signal corresponding to the count of the carryover particles detected by the detectors. Typically the count is determined on the basis of a count rate or count per unit time basis. This information on the carryover particle count may then be used in the control of the operation of the furnace, may be displayed for review by an operator of the furnace, or both.

In connection with displaying the count results from the detectors, the count from each detector may be individually displayed. In addition, the count from all of the detectors may be summed and averaged or otherwise combined to provide an overall indication of the number and/or rate of occurrence of carryover particles. Typically, the overall result is monitored to determine a boiler "upset" condition, that is a condition which results in the production of an abnormal number of carryover particles. Upon a determination that an upset condition is present, the individual detector outputs may be studied to more closely pinpoint the location in the boiler at which the excessive carryover particles are being produced.

To provide corroboration of the results, an image sensor, such as a charge coupled device detector or a large focal point array of photo diodes, is used to produce a visual image of a section of the interior of the boiler and of carryover particles passing therethrough. As a result, an operator of the furnace may visually observe at least a portion of the carryover particles as they are being counted.

As another aspect of the present invention, the signal processor may include a means for establishing a time interval over which a count of carryover particles is obtained. This time interval may be repeated to provide repetitive count rates of carryover particles on a per time interval basis. Alternatively, the time may be measured over which a fixed count of carryover particles occurs, with the results then being converted to a count rate (that is counts per period of time). Other techniques for generating a count rate may also be used, such as simply measuring the amount of time and dividing the observed number of counts by the measured time.

As a subsidiary aspect of the present invention, the signal processor may include an LED or other indicator for providing a visual, auditory or other indication of the occurrence of a detected carryover particle. As a result, confirmation is provided to the operator of the occurrence of carryover particles.

As another aspect of the present invention, the detectors may focus on a focal plane which is a specified distance, such as at least about one foot, from the walls of the furnace. By using a focal plane approach, depth of field detection of carryover particles is possible. That is, only particles within a distance of about twenty percent of the distance from the detector to the focal plane will be detected.

As still another aspect of the present invention, each detector may include a single point detector such as a photo diode for detecting carryover particles, thereby simplifying the electronics of the system. Also, a single point detector is symmetric so that its operation is independent of rotational variations in the position of the detector. Also, such a detector will detect particles equally well regardless of the direction of travel of such particles in a plane perpendicular to the axis of the detector.

As a further aspect of the present invention, information on the count of carryover particles may be used in controlling the performance of the boiler or furnace. The furnace may respond automatically to the count information or semi-automatically, with the furnace operator interactively controlling the furnace in response to the carryover particle count.

The signal processor may also include a microprocessor with a means for compressing the scale or range of the count.

The invention includes the above features taken both individually and in combination with one another.

It is accordingly one object of the present invention to provide an improved apparatus for detecting carryover particles in the interior of a furnace.

Still another object of the present invention is to provide an improved apparatus which may use the detected carryover particle information to, for example, control the operation of the furnace and/or to determine the timing for cleaning deposits from the heat surfaces in the furnace.

These and other objects, features and advantages of the present invention will become apparent with reference to the following description and drawings.

DETAILED DESCRIPTION OF PREFERRED EMBODIMENTS

With reference to FIG. 1, one form of an apparatus for detecting carryover particles in the interior of a furnace 10 is indicated generally at 50. This apparatus includes at least one carryover particle detector 52, and preferably plural such detectors. Each detector has an end 54 positioned, such as being inserted into an existing port of the furnace, for monitoring a portion of the interior of the furnace. These detectors typically include a single point detector, such as a photo diode or other optical detection device. On example of such a detector is a UDT455 photo diode from United Detector Technology. The photo diode is positioned behind a lens for focusing the diode on a region of the furnace of interest. A single point detector, if used, has a number of advantages. For example, such a detector is symmetric in viewing a region of a furnace of interest so that its operation is independent of rotational variations, about the axis of the detector, and is therefore insensitive to such variations as the device is installed. Also, these detectors are equally sensitive to carryover particles traveling in planes perpendicular to the axis of the detector regardless of the direction of travel of carryover particles in such planes. In a conventional manner, the detectors typically include an air purging system for directing purging air across the surface of the lens to sweep debris present in the dusty environment of the furnace away from the lens. Also, the detectors are typically recessed within the ports about one to two inches from the edge of the port so that they do not project into the furnace where they may be impacted by carryover particles.

In FIG. 1, the detector 52 is shown positioned across from a "bull nose" section 46 of the furnace. However, the detectors may be positioned at any suitable location in an upper region of the furnace. In addition, the detectors may all be located in a single plane at distributed locations about the periphery of the walls of the furnace. Alternatively, or in combination, the detectors may be positioned to monitor portions of the interior of the furnace at different elevations, as indicated by the detector 52' in dashed lines in FIG. 1.

In accordance with the present invention, the detectors may be focused substantially at infinity. Due to the opaqueness of the gases typically found within the furnace 10, under these focusing conditions each detector typically focuses on a volume having a length ranging from 0 to about 3 feet away from the side wall of the furnace to which the detector is attached. In such a case, the detectors do not distinguish between particles of a relatively small size which are close to the detector and particles which are of a relatively large size and which are further away from the detector. Alternatively, the detectors may be focused on a focal plane located closer to the side wall of the furnace than with the focus at an infinity focus setting. In this alternative case, depth of field carryover particle discrimination is possible. That is, under these conditions, carryover particles within a certain focal region or distance of the focal plane of a detector, for example within about plus or minus twenty percent of the distance from the wall of the furnace to the focal plane, are in focus and are thus detectable by the detector. In contrast, carryover particles which are closer to the detector than this distance and those that which are farther away tend to be out of focus. Therefore, these signals may be ignored as background noise in the detector output signal. Although the approach of the Herngren patent utilizes an array of detectors focused on a focal plane, in Herngren, et al., as understood by the present inventors, the focal plane is only about 2 to 3 inches away from the adjacent wall of the furnace. The inventors believe that improved detection results from a shift in the focal plane of the detectors to a distance which is at least about one foot from the adjacent side walls of the furnace because this tends to increase the volume of the furnace being sampled to provide a more representative carryover particle count.

A signal processing system 56 is coupled to the detectors, as indicated by lines 58 and 58' in FIG. 1, for receiving the detector output signals and for producing a count signal corresponding to the count of carryover particles detected by the detectors. The detectors produce output signals which are markedly different upon the passage of a carryover particle within the region of the furnace being viewed by a detector. These detector output signals thus contain information on the occurrence of carryover particles. Information from the carryover count may then be displayed or utilized in the control of parameters affecting the performance of the furnace. In particular, signals from the signal processing system 56 may be delivered by a line 60 to the process computer 28 for use in controlling the furnace.

For example, increases in particle count rates have been observed to occur in response to large rapid changes in boiler operating conditions. Also, there may be a correlation between the loading level or volume of the bed 30 and the quantity of carryover particles which is produced. Thus, upon the detection of an excessive carryover particle count, the process computer 28 may act by way of an interface (not shown) and a valve or damper controller 26 to control air dampers 22, 24 and fuel valves 42, 44 in an attempt to reduce the number of generated carryover particles. As one specific example, the air flow dampers 22 and 24 may be opened to increase the air flow and combustion rate to reduce the size of the bed 30. As another specific example, assume that the computer 28 has recently caused a change in the settings of a damper in a manner which produced an unacceptable increase in the carryover particle count rate. In response to the signal on line 60, the process computer 28 may return this damper to its previous condition to minimize the generation of carryover particles.

Figure 2:
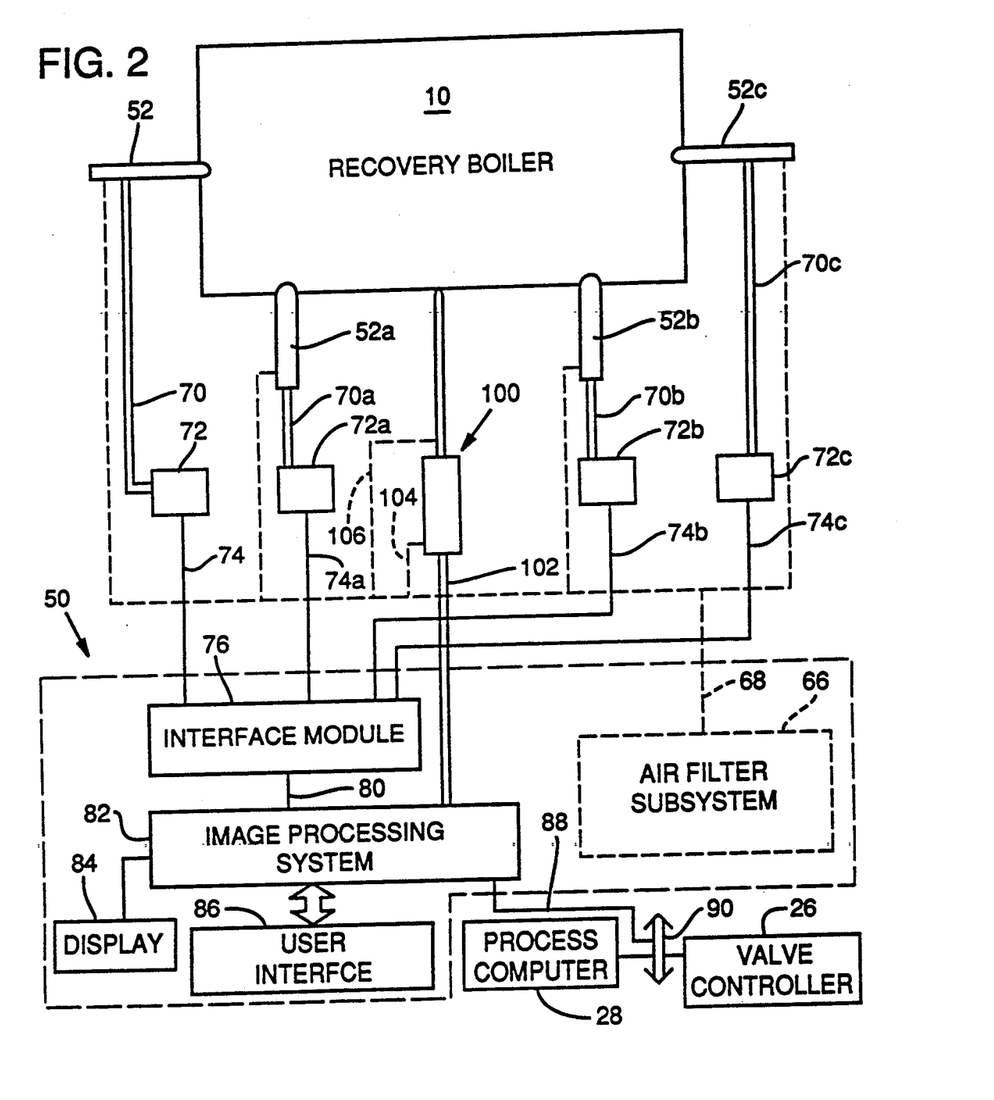
FIG. 2 is a schematic illustration of a carryover particle detection apparatus in accordance with the present invention having plural detectors positioned to detect carryover particles at various locations in a recovery boiler, the illustration also showing one form of a subsystem for controlling the operation of the boiler in response to the detected carryover particle information.

With reference to FIG. 2, one embodiment of the apparatus of the present invention is shown in greater detail. In this case, four detectors 52, 52a, 52b and 52c are positioned at the same elevation of the furnace at spaced apart peripheral locations along three of the sides of the furnace. More or fewer detectors may be used as desired and the detectors may also be located at varying elevations, such as shown in FIG. 1 for detector 52'. In one specific preferred approach, the detectors are in a plane at the "bull nose" level of the boiler at the sides of the boiler other than the "bull nose" side. In general, the detectors are positioned high enough in the furnace to detect burning particles that are likely to still be burning when they reach the upper heat surfaces and tubes of the boiler.

A conventional air filter subsystem 66 filters air and delivers this air through purging lines 68 to the detectors for use in purging or sweeping the lens of each of the detectors. Such an air filter subsystem is also used in the previously described TIPS TM product available from Weyerhaeuser Company.

The output signal from detector 52, and more specifically in the illustrated embodiment from the detector diode, is preprocessed by circuitry at the detector 52, fed by a line 70 to additional preprocessing circuitry 72, and then by a line 74 to a commercially available computer interface module 76 as shown. Similarly, the outputs from detectors 52a, 52b and 52c are fed by way of respective lines 70a, 70b and 70c to associated preprocessing circuits 72a, 72b and 72c and then by respective lines 74a, 74b and 74c to the interface module. Suitable preprocessing circuits are described in greater detail in connection with FIGS. 3 and 4.

The interface module 76 converts the received signals to a suitable digital form for delivery over lines 80 to an image processing subsystem 82. One suitable interface module is an TIPS TM 2000 interface module available from Weyerhaeuser Company. One suitable image processing subsystem is also the TIPS TM system from Weyerhaeuser Company. The imaging processing subsystem 82 includes a display, illustrated separately at 84 in FIG. 2 and a user interface, such as a keyboard, for use in entering information into the image processing subsystem.

The image processing subsystem 82 performs a number of operations on the count data received from the interface module. For example, the image processing system typically sums or otherwise combines the results of the detector counts, which may again be expressed as count rates, from all of the detectors utilized in the system. Then, by way of display 84, the overall average carryover particle counts and trends in overall counts may be displayed. In addition, either alone or in combination with the display of the overall count information, the count from each of the detector locations, in this case the four locations shown in FIG. 2, may also be individually displayed.

With this information, an operator of the boiler 10 may observe an increase in the overall count from all of the detectors. In addition, by then monitoring the individual display of the counts associated with each of the four individual detectors, the operator may determine whether the carryover particle count is increasing generally throughout the furnace or only at selected locations in the furnace. An indication that the carryover count increase is the result of a localized disturbance is implied from a disparate increase in the count from one of the detectors (e.g. 52a) in comparison to the count at the other detectors (e.g. 52, 52b and 52c).

In response to the count information, the boiler operator may enter a command, by way of interface 86, to the image processing subsystem 82 which is passed through another interface module, not shown, and by a line 88 to a data bus 90 and then to the process computer 28. This command results in an adjustment of the performance of the furnace, such as by controlling valve controller 26 to adjust the dampers or valves as previously explained. In addition, the system may operate automatically with count signals being directly sent to the process computer which then determines an appropriate command in response to an increase or decrease in the carryover particle count.

The system of the present invention also facilitates the cross correlation of carryover particle counts to furnace operation parameters. For example, the TIPS TM system is capable of, among other tasks, monitoring the temperature of the bed 30. By correlating temperature changes, or other information on furnace performance, with carryover particle counts, an optimum set of parameters for a particular furnace may be established which minimizes the production of carryover particles. The optimum set of parameters is typically a set of control settings (e.g. fuel flow rate, air flow rate, fuel viscosity, etc.) affecting furnace performance.

In accordance with the present invention, the apparatus may also include an imaging sensor 100 focused on an interior region of the furnace for producing an image signal. This image signal is fed by a line 102 to the image processing subsystem 82 and may also be displayed on display 84. In a conventional manner, the imaging sensor is also typically provided with a source of cooling and purging air, by way of conduits 104, 106, from the air filter subsystem 66. Although any suitable image sensor may be used, typical sensors include a charge coupled device (CCD) detector or a video camera system such as described in U.S. Pat. No. 4,539,588 to Ariessohn, et al. may also be used. The unprocessed image signal on line 102 from the image sensor is digitized by the image processing subsystem 82 and displayed. From this display, the boiler operator may observe the occurrence of carryover particles and compare the observed information to the determined count. This enables the boiler operator, for example, to obtain a visual configuration of the occurrence of at least a portion of the carryover particles being counted by the carryover particle detection system.

With reference to FIGS. 3 and 4A-4C, suitable electronics for use in the apparatus of FIG. 2 will be described. More specifically, light from the field of view of the detector 52, as indicated by arrow 110 in FIG. 3, passes through a small lens and through an optical filter (not shown) and falls upon a ultraviolet-enhanced photo-detector 112. This detector 112 is connected in a photoconductive mode with an integral amplifier 113. The photo diode 112 produces a 0 volt output plus/minus 0.001 volts when the photo diode is not receiving any light. The detector output on line 116 is fed to an optional gain control amplifier 118 with a gain adjustment potentiometer 120.

Figure 3:
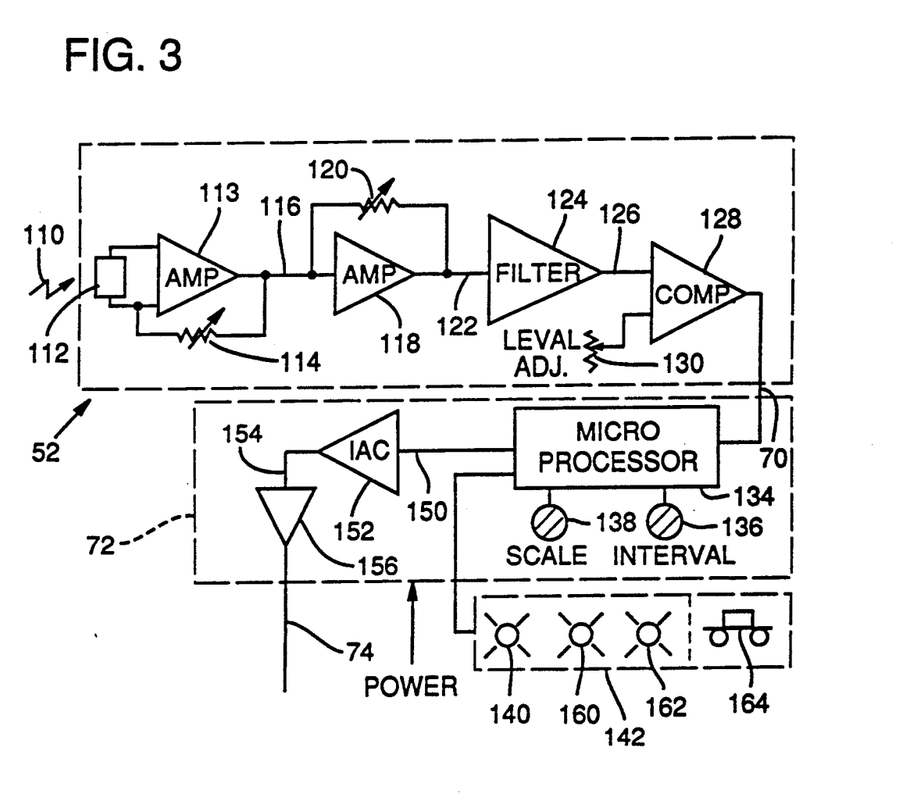
FIG. 3 is an electrical schematic diagram of one form of circuit usable in conjunction with the detectors of FIGS. 1 and 2.

The average analog value of the signals in this specific circuit should not exceed plus/minus 7 volts relative to ground potential (0 volts). Peak voltages also should typically not exceed about 10 volts in this specific circuit. Optimum performance is typically achieved when the average analog values are about 2 to 3 volts above ground potential. The object of these settings is to avoid the saturation of the optical detector. The value of the analog output from the amplifier 113 is adjusted by replacing the optical filter with a higher or lower value to achieve these operating conditions.

Figure 4A:
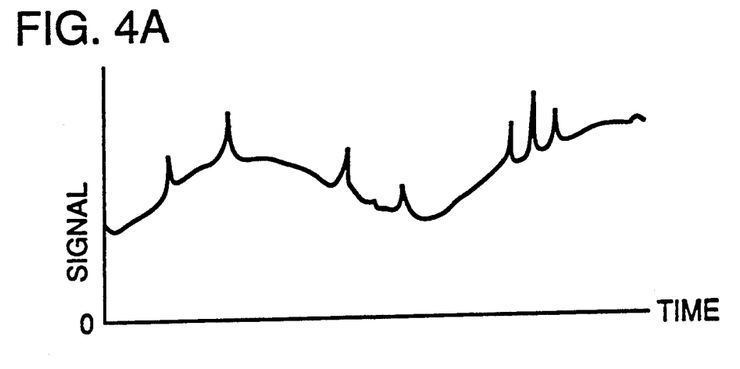
FIG. 4A, 4B and 4C illustrate representative signals at selected points in the circuit of FIG. 3.

The signal from amplifier 118 is fed on a line 122 to a high pass filter 124. An exemplary signal on line 122 is shown at FIG. 4A and includes gradually varying background or noise signals, resulting from varying background light in the furnace, along with peaks indicative of the occurrence of carryover particles. The filter 124 minimizes the affect of these slowly varying background changes as indicated by the filtered signal shown in FIG. 4B. The filter typically comprises a 24 db per octave high pass filter, with a 3 db cut-off frequency of 3 Hz. This filter removes most of the background radiation from the detected signal.

Figure 4B:
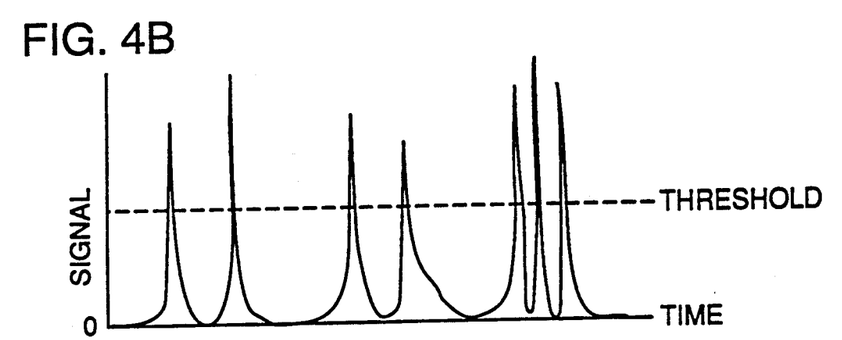
Figure 4C:
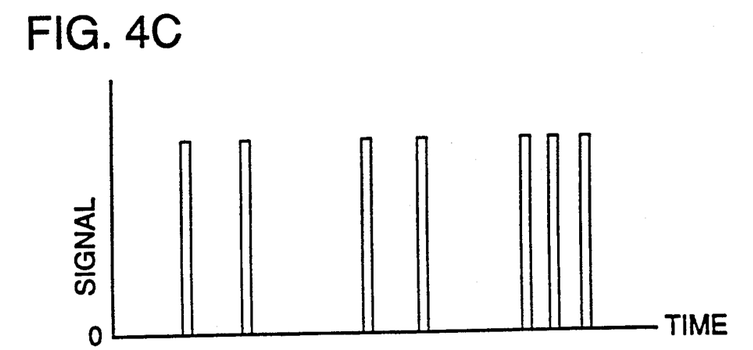

The filter output is fed by a line 126 to a first input of a comparator 128. A reference voltage circuit 130 is coupled to the comparator 128 for providing a reference or threshold voltage signal for the comparator. As shown in FIG. 4B, the threshold level is adjusted to eliminate or minimize the effect of background noise on the detected carryover pulses. A typical threshold for this circuit is approximately 0.5 to 1.0 volts above the peak noise levels. The comparator illustrated in FIG. 3 outputs a logic "0" when the threshold, set by the threshold or level adjust potentiometer 130, is exceeded. When the signal drops below the threshold, the output of the comparator returns to logic "1." An exemplary inverted output from the comparator 128 is shown in FIG. 4C. The components described with reference to FIG. 3 to this point are typically packaged as a printed circuit board and included within the detector 52.

The comparator output appears on line 70 and is typically coupled to a circuit 72 on a circuit board which is spaced from the detectors. The components on circuit 72 are thus more isolated from the adverse heat and other environmental conditions associated with the furnace. The signal on line 70 is fed to a count detection input of a microprocessor 134. The pulses received on the input pin to the microprocessor are counted. Although a single microprocessor with plural inputs may be used for receiving the signals from all of the detectors, more typically a separate microprocessor is associated with each detector.

An interval switch, indicated at 136 in FIG. 3, may be used to establish a time interval over which carryover particles are counted. When the interval selected by this interval switch has ended, the carryover particle counter value and the interval setting may be read by a microprocessor scaling routine to provide count rate information on a per unit time basis. These time intervals may be repeated to provide counts on a per interval basis as well. Alternatively, the amount of time required for a specific number of counts to occur may be measured with the counts number and then being divided in the microprocessor by this measured time to produce a count rate. In general, when a count in the form of a count rate is desired, a mechanism is employed which produces a result expressed in units of counts per time. In the interval approach, the scaling routine divides the count value by the interval setting and uses a full scale setting (set by a scale switch 138) to create an 8-bit number. If the result exceeds 8-bits, an overflow indicator, such as an LED 140 on display board 142, is activated and the 8-bit value (or other count rate indicator) is set to 255, a full scale output. The 8-bit value is transmitted over a line 150 to a digital-to-analog converter 152. In addition, the digital-to-analog converter output is fed over a line 154 to a driver 156, such as a 1B21 optical isolating driver from Analog Devices. The output of driver 156, on line 74, is at a suitable level for delivery to the interface module 76 (FIG. 2). For example, in a typical pulp mill, signals at a 4 ma. level (corresponding to a zero output) and a 20 ma. level (corresponding to a full-scale output) are used. Another common mill scale range is from zero to 10 volts. For such mills, the output of driver 156 is adjusted for this latter scale.

A full-scale output occurs typically when the average number of detected carryover particles per second equals or exceeds the setting of the scale switch 138. For example, for a scale switch position of zero, the maximum average of detected carryover particles per second may be one; for a scale switch position of one, a maximum average of detected carryover particles per second may be two; for a scale switch position of two, the maximum average is five; for a scale switch position of three, the maximum average is ten; for a scale switch position of four, the maximum average is 20; for a scale switch position of five, the maximum average is 50; and for a scale switch position of six, the maximum average is 100. Also, typical time intervals established by interval switch 136 are respectively 1 second, 2 seconds, 5 seconds, 15 seconds, 30 seconds, 1 minute, 2 minutes, 5 minutes, and 15 minutes.

The interval switch 136 is typically eliminated by simply measuring the amount of time required to achieve a carryover particle count of a particular magnitude and dividing the count by the measured time. Also, the scale switch 138 is also typically eliminated by providing the microprocessor with a mechanism for compressing the scale. For example, by expressing the count rate on a logrithmic scale in the microprocessor, the count rate may be accommodated without the occurrence of an overload condition.

The display panel 142 may also include indicators 160, 162 for other purposes. For example, indicator 160 may comprise an LED or other visual or auditory indicator which is activated, for example, for 1/30th of a second, to indicate that a carryover particle has been detected. In addition, the indicator 162, such as an LED, may be used to indicate the end of each interval if a times interval approach is being used. Also, a reset switch 164 may be provided to reset the microprocessor to a zero count.

The information on carryover particle counts may be displayed for observation by an operator of the boiler to verify boiler performance. In addition, this information may also optionally be used in the control of parameters, such as fuel and air flow, affecting boiler performance.

Having illustrated and described the principles of our invention with respect to several preferred embodiments, it should be apparent to those of ordinary skill in the art that our invention may be modified in arrangement and detail without departing from such principles. For example, the electronic circuitry used to obtain a count of carryover particles may be substantially modified while still performing this function. We claim as our invention all such modifications which fall within the scope of the following claims.

We claim:

1. An apparatus for detecting carryover particles in the interior of a furnace comprising:
   plural spaced apart carryover particle detectors each directed toward a different region of the interior of the furnace for detecting the presence of carryover particles in such regions of the furnace interior, the detectors producing output signals upon the detection of carryover particles;
   a signal processor coupled to the detectors for receiving the output signals and for producing a count signal corresponding to the count of the carryover particles detected by the detectors.

2. An apparatus according to claim 1 including a display means for receiving the count signal and for displaying a count of the carryover particles, the display means also comprising means for individually displaying the count of carryover particles from each of the regions of the furnace monitored by the detectors.

3. An apparatus according to claim 1 also including imaging sensor means focused on an interior region of the furnace for producing an image signal and means for displaying the image signal so as to allow a user to visually observe at least a portion of the carryover particles being counted.

4. An apparatus according to claim 1 in which the signal processing means includes means for establishing a time interval over which a count of carryover particles is obtained, the signal processing means providing a count of carryover particles on a per time interval basis.

5. An apparatus according to claim 1 in which the signal processing means comprises means for measuring the time over which a count of carryover particles occurs and for dividing the count by the measured time to produce a count rate.

6. An apparatus according to claim 1 in which the signal processing means includes indicator means for producing a visual indication of the occurrence of each detected carryover particle.

7. An apparatus according to claim 1 in which the furnace has a wall and each detector is focused on a focal plane which is at least about one foot from the wall of the furnace.

8. An apparatus according to claim 1 wherein each detector includes a single photo diode for detecting carryover particles.

9. An apparatus according to claim 1 including means for controlling the furnace in response to the count of the carryover particles.

* * * * *